(12) United States Patent
Grimm et al.

(10) Patent No.: US 6,932,823 B2
(45) Date of Patent: Aug. 23, 2005

(54) DETACHABLE SUPPORT ARM FOR SURGICAL NAVIGATION SYSTEM REFERENCE ARRAY

(75) Inventors: James E. Grimm, Winona Lake, IN (US); Shawn E. McGinley, Fort Wayne, IN (US)

(73) Assignee: Zimmer Technology, Inc., Chicago, IL (US)

( * ) Notice: Subject to any disclaimer, the term of this patent is extended or adjusted under 35 U.S.C. 154(b) by 0 days.

(21) Appl. No.: 10/603,007

(22) Filed: Jun. 24, 2003

(65) Prior Publication Data

US 2004/0267242 A1 Dec. 30, 2004

(51) Int. Cl.⁷ .............................................. A61B 19/00
(52) U.S. Cl. ........................ 606/130; 128/898; 606/96
(58) Field of Search ......................... 606/130, 96–100; 128/898

(56) References Cited

U.S. PATENT DOCUMENTS

| | | | |
|---|---|---|---|
| 5,007,936 A | 4/1991 | Woolson ....................... 623/23 |
| 5,230,338 A | 7/1993 | Allen et al. .................. 128/653 |
| 5,251,127 A | 10/1993 | Raab |
| 5,305,203 A | 4/1994 | Raab |
| 5,551,429 A | 9/1996 | Fitzpatrick et al. ....... 128/653.1 |
| 5,622,170 A | 4/1997 | Schulz ..................... 128/653.1 |
| 5,682,886 A | 11/1997 | Delp et al. ................ 128/653.1 |
| 5,682,890 A | 11/1997 | Kormos et al. ........... 128/653.2 |
| 5,732,703 A | 3/1998 | Kalfas et al. |
| 5,772,594 A | 6/1998 | Barrick ....................... 600/407 |
| 5,871,018 A | 2/1999 | Delp et al. .................... 128/898 |
| 5,904,691 A | 5/1999 | Barnett et al. |
| 5,913,820 A | 6/1999 | Bladen et al. .............. 600/407 |
| 5,921,992 A | 7/1999 | Costales et al. |
| 5,995,738 A | 11/1999 | DiGioia, III |
| 6,002,859 A | 12/1999 | DiGioia, III |
| 6,021,343 A | 2/2000 | Foley et al. |
| 6,059,832 A | 5/2000 | Memon |
| 6,190,395 B1 | 2/2001 | Williams |
| 6,235,038 B1 | 5/2001 | Hunter et al. |
| 6,236,875 B1 | 5/2001 | Bucholz et al. |
| 6,285,902 B1 | 9/2001 | Kienzle, III et al. |
| 6,306,146 B1 * | 10/2001 | Dinkler ....................... 606/130 |
| 6,328,748 B1 * | 12/2001 | Hennig ........................ 606/130 |
| 6,348,058 B1 | 2/2002 | Melkent et al. |
| 6,368,331 B1 * | 4/2002 | Front et al. .................. 606/130 |
| 6,381,485 B1 * | 4/2002 | Hunter et al. ............... 600/407 |
| 6,402,762 B2 | 6/2002 | Hunter et al. |
| 6,430,434 B1 | 8/2002 | Mittelstadt .................. 600/426 |
| 6,434,507 B1 | 8/2002 | Clayton et al. |
| 6,450,978 B1 | 9/2002 | Brosseau et al. |
| 6,470,207 B1 | 10/2002 | Simon et al. ............... 600/426 |

(Continued)

*Primary Examiner*—Roy D Gibson
*Assistant Examiner*—Henry M Johnson, III
(74) *Attorney, Agent, or Firm*—Jonathan Feuchtwang Baker & Daniels

(57) ABSTRACT

A detachable support arm structure couples a computer-assisted navigation system reference array to an instrument, for example, a surgical instrument, such that the geometry between the reference array and the surgical instrument is predetermined and registration of the instrument in the navigation system does not require calibration each time the reference array and support arm structure are coupled to the instrument. The support arm structure includes a mounting interface engageable with a mounting interface on the instrument. Engagement of the mounting interfaces releasably secures and repeatably and accurately locates and fixes the support structure to the instrument in a predefined geometry in each of six degrees of freedom. The reference array includes at least one reference element and is releasably securable to the support structure in a predefined geometry of the support structure relative to the reference array which repeatably and accurately locates and fixes the support structure relative to the reference array in each of six degrees of freedom.

26 Claims, 12 Drawing Sheets

U.S. PATENT DOCUMENTS

| | | |
|---|---|---|
| 6,474,341 B1 | 11/2002 | Hunter et al. ............... 128/899 |
| 6,477,400 B1 | 11/2002 | Barrick |
| 6,490,467 B1 | 12/2002 | Bucholz et al. |
| 6,491,699 B1 | 12/2002 | Henderson et al. |
| 6,493,573 B1 | 12/2002 | Martinelli et al. .......... 600/424 |
| 6,499,488 B1 | 12/2002 | Hunter et al. ............... 128/899 |
| 6,556,857 B1 | 4/2003 | Estes et al. |
| 6,725,080 B2 * | 4/2004 | Melkent et al. ............. 600/424 |
| 2001/0034530 A1 | 10/2001 | Forst et al. |
| 2003/0069591 A1 | 4/2003 | Smothers et al. |

* cited by examiner

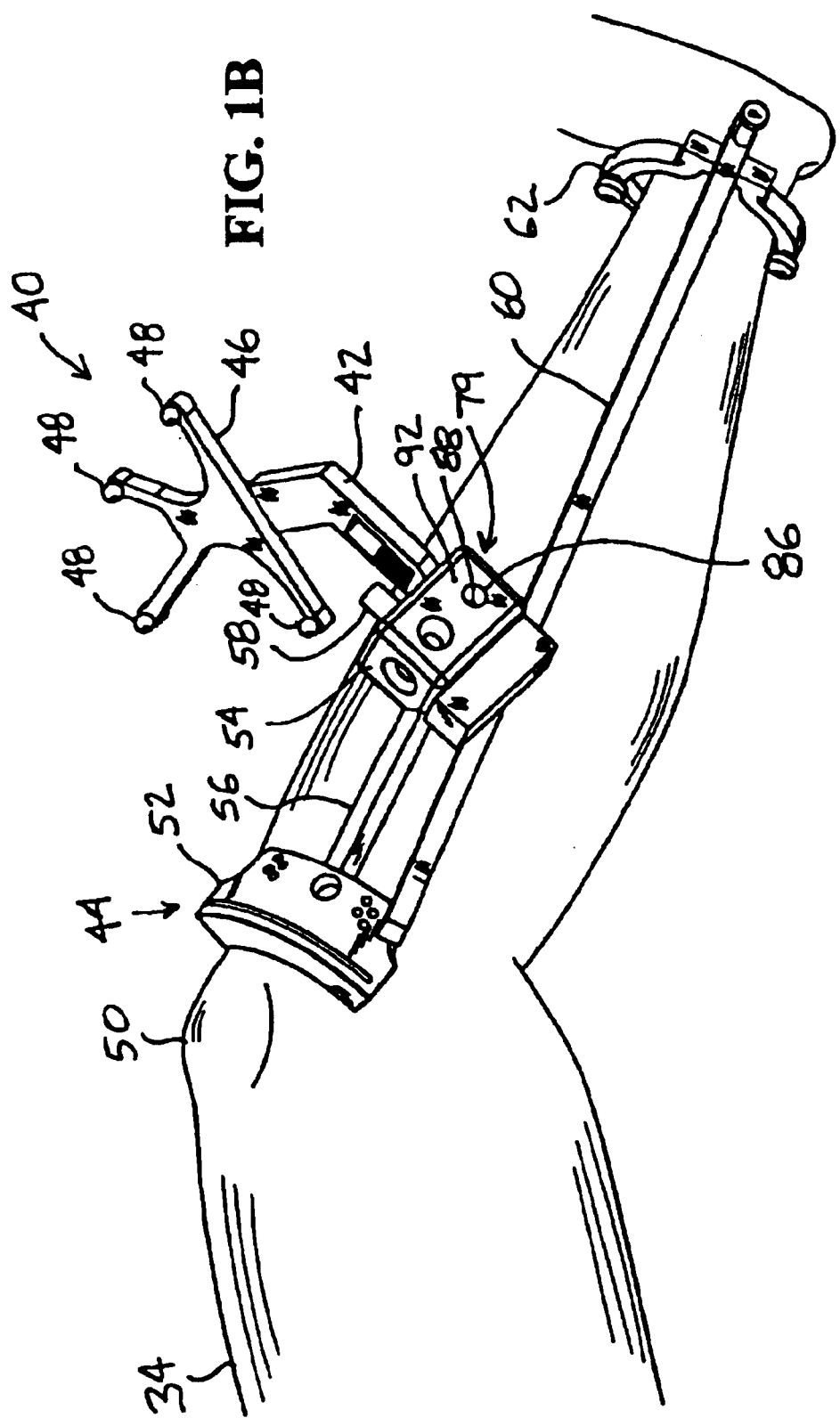

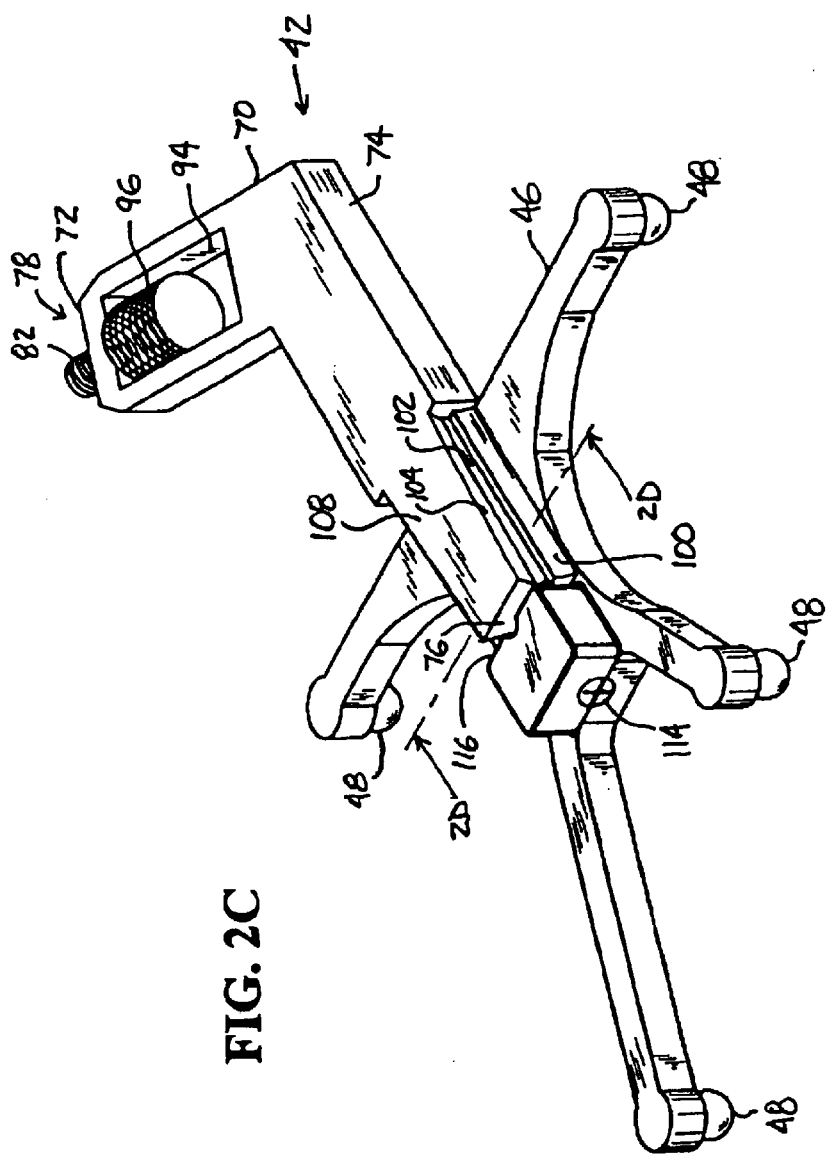
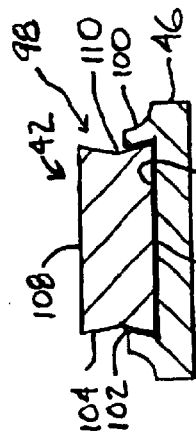
FIG. 2C
FIG. 2D

DETACHABLE SUPPORT ARM FOR SURGICAL NAVIGATION SYSTEM REFERENCE ARRAY

BACKGROUND

The present invention relates to computer-assisted navigation and, more specifically, to a detachable support arm which may be used to couple a computer-assisted navigation reference array to an instrument.

The controlled positioning of surgical instruments is of significant importance in many surgical procedures. Various methods and guide instruments have been developed for properly positioning a surgical instrument. Such instruments and methods include the use of surgical guides which are properly positioned in relation to one or more anatomical structures and function as mechanical guides for surgical instruments such as, e.g., cutting, reaming, and drilling instruments. The use of such surgical guides is common in orthopedic surgical procedures, and such guides may be used to properly locate and align a surgical instrument with respect to a bone when preparing the bone for receiving an implant such as an artificial joint. Positioning relative to the bone has typically been aided by using intramedullary instrument systems. Intramedullary systems utilize instruments placed within the structure of a bone, for example the intramedullary canal. The instruments provide a temporary positioning reference relative to the bone anatomy.

The advent of minimally invasive surgery has increased the requirement for inventive positioning systems to replace intramedullary systems, for example, computer-assisted navigational systems, as described below, and extramedullary frames and alignment devices, such as the one disclosed in "Method and Apparatus for Achieving Correct Limb Alignment in Unicondylar Knee Arthroplasty," U.S. patent application Ser. No. 10/305,697, filed Nov. 27, 2002, the disclosure of which is hereby incorporated herein by reference.

Computer-assisted navigational techniques often involve acquiring preoperative images of the relevant anatomical structures and generating an anatomical coordinate system database which represents a three-dimensional model of the anatomical structures. The relevant surgical instruments typically have a known and fixed geometry which is also defined in the database preoperatively. During the surgical procedure, the position of the instrument being used and the location of one or more nearby anatomical landmarks are registered with the anatomical coordinate system by employing a position sensing system capable of locating instruments and landmarks in all six degrees of freedom. A graphical display showing the relative position of the instrument and anatomical structures may then be computed in real time and displayed for the surgeon to assist in properly positioning and manipulating the surgical instrument with respect to the relevant anatomical structures.

In such image-guided procedures, a robotic arm may be used to position and control the instrument, or the surgeon may manually position the instrument, and use the display of the relative position of the instrument and anatomical structure to properly position the instrument. Examples of various computer-assisted navigation systems are described in U.S. Pat. Nos. 5,682,886; 5,921,992; 6,096,050; 6,348,058 B1; 6,434,507 B1; 6,450,978 B1; 6,490,467 B1; and 6,491,699 B1. The disclosures of each of these patents are hereby incorporated herein by reference.

Surgical instruments have typically been adapted for use with computer-assisted navigation systems by clamping a position reference array that is registrable in the navigation system onto the surgical instrument at an arbitrary position and orientation relative to the instrument. Because the position and orientation is arbitrary, the geometric relationship between the reference array and the surgical instrument must then be calibrated in order to register the combination of the reference array and the surgical instrument in the navigation system and to properly graphically display the relative position of the instrument to the anatomical structure. Thus, each time the reference array is coupled to a surgical instrument, the combination must again be carefully calibrated and registered to ensure the graphical display viewed by the surgeon on the computer-assisted navigation system reflects the actual position and orientation of the instrument relative to the anatomical structure.

The variability associated with arbitrarily clamping a reference array to a surgical instrument and the possibility of a clamped reference array slipping relative to the surgical instrument causes uncertainty in the geometry of the combination, thus requiring careful and possibly repeated instrument calibrations. Surgical tools which include a reference array permanently affixed eliminate the uncertainty of the geometry and repeated calibration and registration in the navigation system; however, a surgical tool so equipped may then not be suitable for procedures which require the array to be in a different position relative to the instrument or may not be suitable for use without the computer-assisted navigation system because of the reference array that is permanently affixed to it.

SUMMARY OF THE INVENTION

The present invention includes a detachable support arm structure for coupling a computer-assisted navigation system reference array to an instrument, for example, a surgical instrument, such that the geometry between the reference array and the surgical instrument is predetermined. By using a predefined geometry, registration of the instrument in the navigation system does not require calibration each time the reference array and support arm structure are coupled to the instrument.

In one exemplary embodiment, the support structure includes a mounting interface that is engageable with a mounting interface on the instrument. Engagement of the mounting interfaces releasably secures the support structure to the instrument in a predefined position in each of six degrees of freedom relative to the support structure thereby fixing the geometry of the support structure relative to the instrument in each of the six degrees of freedom. Predefined position is defined as a predetermined location and orientation in all six degrees of freedom which is accurately repeatable. Thus, each time the support structure is coupled to the instrument, the support structure and instrument accurately and repeatably form the same predefined geometry.

In one exemplary embodiment, the reference array includes at least one reference element and is releasably securable to the support structure. The reference array secures to the support structure in a predefined position and orientation in each of six degrees of freedom. Thus, each time the reference array is coupled to the support structure, the array and support structure accurately and repeatably form the same predefined geometry. Additionally, the coupling of the support structure to both the instrument and reference array forms a predefined geometry that is accurate and repeatable in each of six degrees of freedom.

The support structure, comprising a support arm in the exemplary embodiment, for a reference array may be used to adapt instruments for use with computer-assisted navigation systems. Although the support structure may be used for instruments used in a wide range of fields, for example, medicine, biology, electronics, micromachinery, and other such fields requiring accurate positioning of tools or instruments, the support structure is hereinafter described with reference to surgical instruments and computer-assisted surgical navigation systems.

Various exemplary embodiments of the support arm structure are contemplated. Certain exemplary embodiments include a mounting interface that is engageable with a companion mounting interface on a surgical instrument. Additionally, the support arm supports at least one reference element that is registrable in the computer-assisted navigation system. In one exemplary embodiment, the reference elements are disposed on a reference array that includes at least three reference elements, the array being releasably securable to the support arm structure.

Advantageously, the support arm, reference array, and instrument, as well as the combination thereof, all have a predefined geometry that is registered with the navigation system. The mounting interfaces connecting the support arm structure to the instrument and the reference array to the support arm structure accurately and repeatably locate and orient the components relative to one another such that upon coupling the reference array to the support arm structure and the support arm structure to the instrument, the predefined geometry is formed. Advantageously, the predefined geometry for an instrument and the associated support structure and reference array may be supplied to the navigation system once and then retained by the navigation system. Therefore, each time a support arm structure is recoupled with an instrument, the assembly does not need to be recalibrated with the navigation system, rather the assembly only need be verified to ensure a component has not been bent or otherwise damaged, thus altering the predefined geometry known to the computer-assisted navigation system.

Exemplary embodiments of a detachable support arm for a surgical navigation system reference array include those having a dovetailed mounting surface and threaded fastener receptacle that may be used to lockingly engage a reference array in a predefined and accurately repeatable manner. Additionally, certain support arm structures in accordance with the present invention include a mounting interface for releasably engaging the instrument and which allows for accurate repeatable coupling of the support arm to the instrument to ensure that a predefined geometric relationship between the support arm and instrument is provided upon each coupling.

In certain exemplary embodiments, the mounting interface between the support arm structure and the instrument includes a cannulated cylindrical boss having a threaded fastener extending therethrough for locating and fixing the support arm structure to a mating interface on the instrument. The mounting interface can further include a small cylindrical pin for locating the support arm structure rotationally relative to the axis formed by the cylindrical locating boss. Thus, once the cylindrical boss and locating pin are engaged in matching receptacles in the instrument and the threaded fastener is engaged into a threaded receiving hole in the instrument, the support arm structure is accurately positioned in the predefined geometry relative to the instrument.

Advantageously, the support arm structure may define a length, bend, curve, or other geometry such that the reference array is displaced in a desirable position relative to the instrument so as to not hinder the surgeon's use or interfere with nearby anatomical structure or other instrumentation. Additionally, the support arm structure's geometry positions the reference array to provide the necessary orientation and line of sight with the navigation system sensors for accurate registration in and use with the navigation system.

Embodiments of the support arm structure may be designed for a specific surgical instrument, for example, a distal femoral cut guide, a profile femoral cut guide, and a proximate tibial cut guide as are used in partial or total knee arthroplasty. Such a procedure is disclosed by a paper on an intramedullary surgical approach for a partial knee arthroplasty entitled "The M/G™ Unicompartmental Knee Minimally Invasive Surgical Technique," available from Zimmer, Inc., of Warsaw, Ind., the disclosure of which is hereby incorporated herein by reference. Alternatively, the support arm structure may be designed for use with more than one surgical instrument.

Advantageously, one embodiment of the support arm structure is designed to engage either of two mounting interfaces associated with a proximal tibial cut guide and includes a double dovetail mounting interface for the reference array. The plurality of predefined geometries that may be formed by selecting which interfaces to couple allow the support arm structure to be used for both medial and lateral approaches for proximal tibial preparation in a total or partial knee arthroplasty.

A first exemplary embodiment of the present invention includes an apparatus usable with a computer-assisted navigation system, the apparatus including an instrument; a support structure releasably exchangeable with the instrument in a first predefined position; and at least one reference element disposed with the support structure in a second predefined position, the at least one reference element being registrable in the computer-assisted navigation system; the first and second predefined position and the support structure comprising a first geometry of the at least one reference element relative to the instrument in each of six degrees of freedom.

In another embodiment, a system usable with a computer-assisted navigation system is provided, the system including a plurality of instruments; a support structure engageable with each of the plurality of instruments wherein engagement of the support structure with a selected one of the plurality of instruments releasably secures the support structure to the selected one of the plurality of instruments in a first predefined position; and at least one reference element disposed with the support structure in a second predefined position, the at least one reference element being registrable in the computer-assisted navigation system; the first and second predefined position and the support structure comprising a first predefined geometry of the at least one reference element relative to the one of the plurality of instruments in each of six degrees of freedom.

In yet another embodiment, a method of preparing an instrument is provided, the instrument having a first predefined geometry for registration in a computer-assisted navigation system, the method including the steps of providing a support structure which is accurately and releasably engageable to the instrument in a second predefined geometry relative to the instrument; providing a reference array having at least one reference element disposed therewith, the reference element having a third predefined geometry and being registrable in the computer-assisted navigation system; releasably coupling the support structure to the instrument; releasably coupling the reference array to the support structure in a fourth predefined geometry wherein the first, second, third, and fourth geometry define a known spatial relationship of the at least one reference element and the instrument in the computer-assisted navigation system.

BRIEF DESCRIPTION OF THE DRAWINGS

The above mentioned and other features and objects of this invention, and the manner of attaining them, will become more apparent and the invention itself will be better understood by reference to the following description of embodiments of the invention taken in conjunction with the accompanying drawings, wherein:

FIG. 1B is a partial perspective view of the surgical arrangement of FIG. 1A showing a surgical apparatus including the detachable support arm;

FIGS. 2A, 2B, 2C, and 2E are perspective views of a first exemplary embodiment support arm structure according to the present invention;

FIG. 2D is a cross-sectional view of the first exemplary embodiment of FIG. 2C;

Figure 1A:
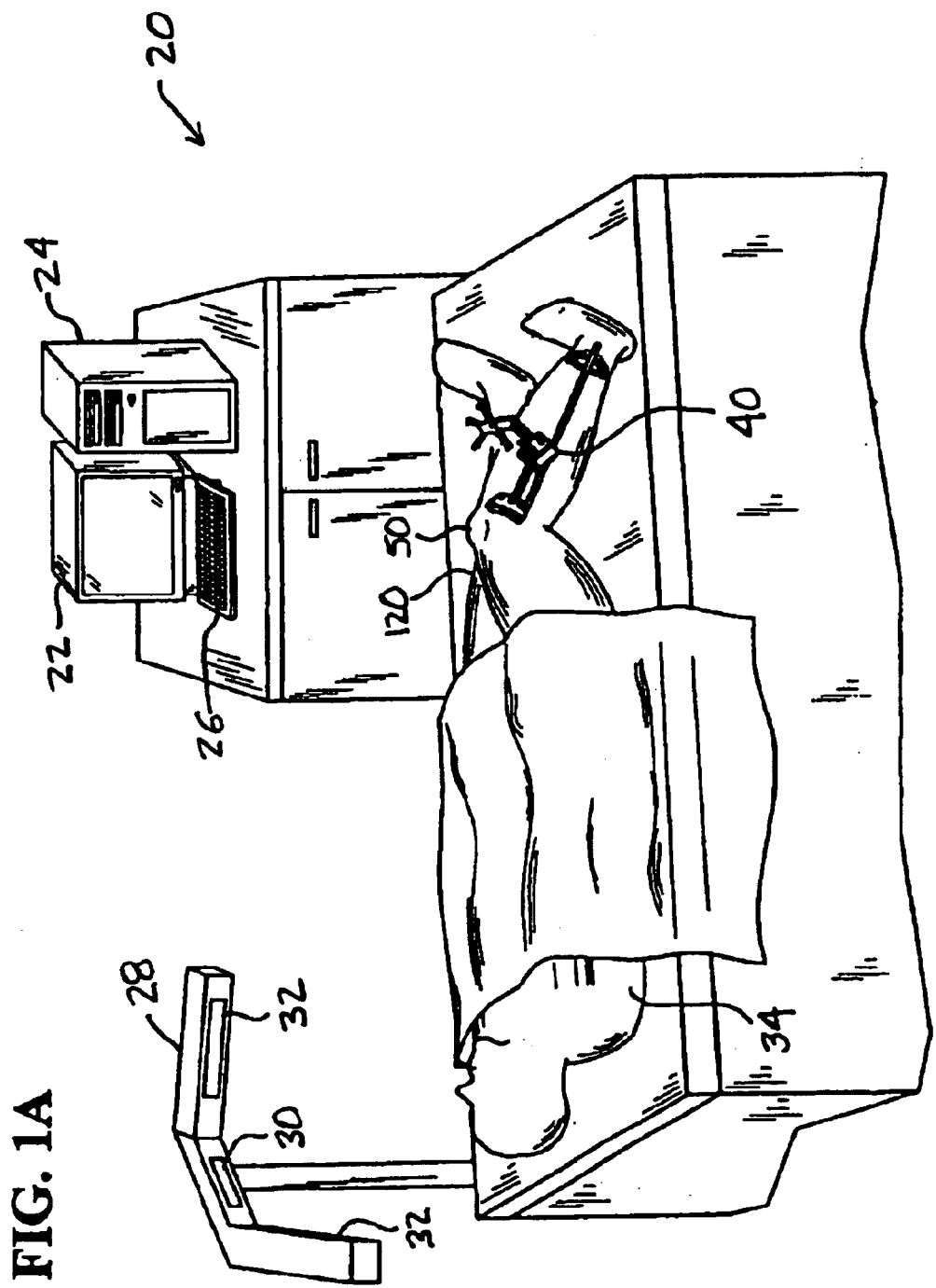
FIG. 1A is a perspective view of an operating room arrangement having a computer-aided navigation system utilizing a detachable support arm for a surgical navigation system reference array in accordance with the present invention.

Corresponding reference characters indicate corresponding parts throughout the several views. Although the drawings represent embodiments of the present invention, the drawings are not necessarily to scale and certain features may be exaggerated in order to better illustrate and explain the present invention. The exemplification set out herein illustrates embodiments of the invention, in several forms, and such exemplifications are not to be construed as limiting the scope of the invention in any manner.

DESCRIPTION OF THE INVENTION

The embodiments disclosed below are not intended to be exhaustive or limit the invention to the precise forms disclosed in the following detailed description. Rather, the embodiments are chosen and described so that others skilled in the art may utilize their teachings.

FIG. 1A shows an operating room arrangement having computer-assisted navigation system 20 for aiding surgical procedures performed on patient 34. Apparatus 40 is usable with computer-assisted navigation system 20 and, referring to FIG. 1B, more specifically includes support arm structure 42 for coupling surgical instrument 44 and navigation system reference array 46.

Computer-assisted navigation system 20 (FIG. 1A) is used to provide a graphical representation of the position of surgical instrument 44 (FIG. 1B) or another medical instrument relative to the anatomical structures of patient 34. Navigation system 20 may include display 22, CPU 24, keyboard 26 and reference locator 28. Generally, CPU 24 and reference locator 28 determine the position and orientation of surgical instrument 44 by detecting the position and orientation of connected navigation system reference array 46 and knowing the geometry of array 46 and instrument 44. Display of a graphical image to represent the current position of instrument 44 may be overlaid on a fluoroscopic image of anatomical structures of patient 34 on display 22. Such a computer-assisted navigation system is described in the disclosure of U.S. Pat. No. 6,470,207 B1 which is hereby incorporated herein by reference.

Computer-assisted navigation systems are known in the art which provide for the registration of anatomical structures of patient 34 with a three-dimensional model representing the structure. Calibration for localization of instrument 44 facilitates the display of the relative positions of instrument 44 and anatomical structures, for example, the exemplary systems disclosed by U.S. Pat. Nos. 6,236,875 B1 and 6,167,145, and U.S. patent application to Grimm et al. entitled "Implant Registration Device for Surgical Navigation System," Ser. No. 10/357,754, filed Feb. 4, 2003, the disclosures of which are hereby incorporated herein by reference.

A tracking device such as navigation system reference array 46, shown in FIGS. 1A and 1B, enables the calibration and localization of surgical instrument 44 and the tracking of the instrument motion with respect to anatomical structures of patient 34, which has also been located by navigation system 20. In certain exemplary embodiments, reference locator 28, shown in FIG. 1A, includes emitter 30 and sensors 32 for illuminating and detecting the location of reference elements 48 (FIG. 1B) which are arranged non-linearly on navigation system reference array 46. For example, emitter 30 may direct infrared light toward reference elements 48. Reference elements 48 passively reflect the light and are detected and positionally located by sensors 32, thereby allowing processor 24 to calculate the position and orientation of surgical instrument 44 for display relative to an image of the anatomical structures of patient 34 on display 22. In one exemplary embodiment, sensors 32 are charged couple devices.

In order to provide computer-assisted navigation for instrument 44, reference array 46 is fixed relative to instrument 44. For example, for minimally invasive total knee arthroplasty, various instruments including cutting guides must be located relative to anatomical landmarks, e.g., the mechanical axis of the femur and tibia, in order to prepare the femur and tibia for a knee arthroplasty. Such a procedure is described in "The M/G™ Unicompartmental Knee Minimally Invasive Surgical Technique," available from Zimmer, Inc., of Warsaw, Ind., the disclosure of which is hereby incorporated herein by reference.

Referring to FIG. 1B, surgical instrument 44 is depicted as a proximal tibial cutting guide located just below knee 50 of patient 34 and is useful for guiding a reciprocating saw blade used for preparing the tibial plateau to receive an implant device. The exemplary surgical instrument 44 includes cutting guide 52, block 54, and stem 56. Cutting guide 52 is coupled to mounting block 54 by stem 56 and may be held in position by pin 58 of extramedullary frame 60 which is coupled to patient 34 by clamp 62.

Figure 2A:
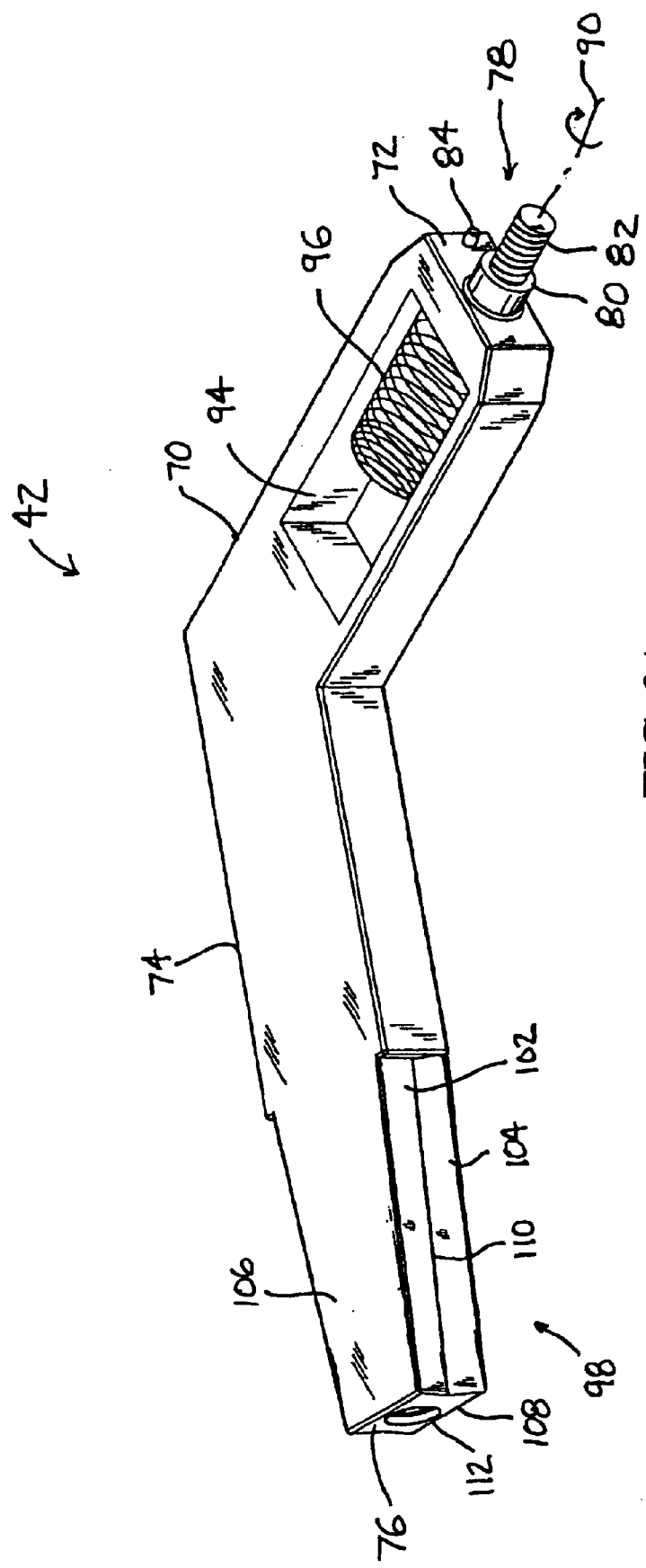
Figure 2B:
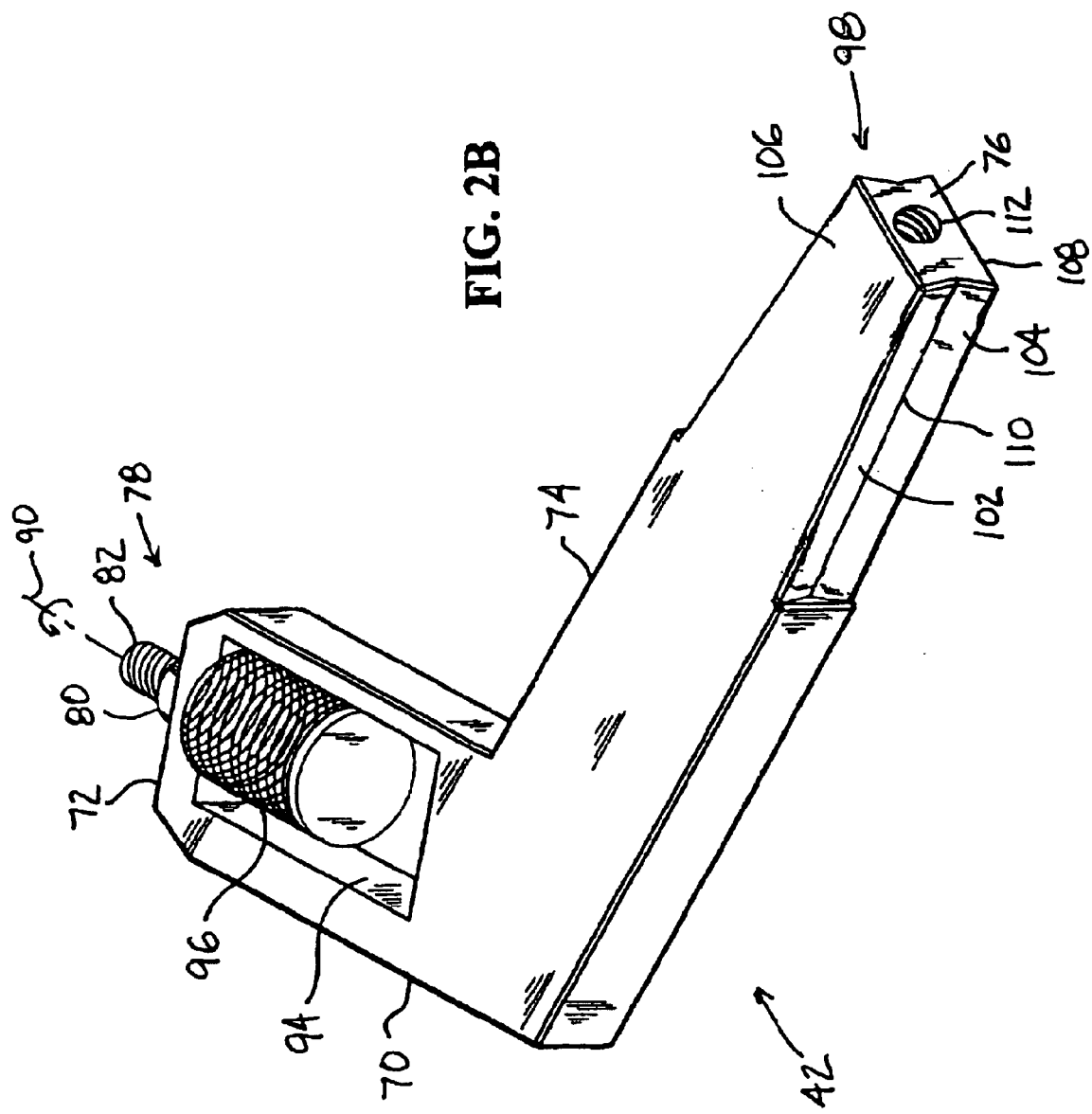

Advantageously, inventive support arm structure 42, the first embodiment of which is also shown in FIGS. 2A and 2B, releasably couples reference array 46 to instrument 44, thereby allowing for real-time graphical positioning of cutting guide 52 relative to anatomical structures of patient 34 by viewing the images displayed on display 22 (FIG. 1A) of navigation system 20.

First embodiment support arm structure 42 advantageously provides a predefined geometry when coupled with surgical instrument 44 and reference array 46. Support structure 42 may be used to repeatably and accurately couple reference array 46 to surgical instrument 44, each time providing the same geometry in all six degrees of freedom and eliminating degrees of uncertainty.

Additionally, support arm structure 42 allows for adaptation of traditional surgical instruments for dual use for traditional and computer-assisted surgical techniques. Advantageously, support arm structure 42 is sized and shaped to position reference array 46 conveniently away from cutting guide 52 and anatomical structures of patient 34 while orienting reference array 46 within line-of-sight of and for accurate positioning by reference locator 28 (FIG. 1A). First embodiment support arm structure 42 positions reference array 46 above and medially from cutting guide 52 in a position that does not encumber cutting or interfere with anatomical structures of patient 34.

Referring to FIGS. 2A and 2B, support arm structure 42 includes first extension portion 70 defining first end 72 and second extension portion 74 oriented approximately 45° relative to first extension portion 70 and defining second end 76. First end 72 includes instrument mounting interface 78 for removably coupling support arm structure 42 to one of mounting interfaces 79 of instrument 44 (one of which is shown in FIG. 1B, the other of which support arm 42 is shown coupled to). Instrument mounting interface 78 is configured to accurately and repeatably position and couple support arm structure 42 to instrument 44 in all six degrees of freedom. In the exemplary embodiments, instrument mounting interface 78 includes boss 80, threaded fastener 82, and rotational locating pin 84. However, other configurations providing positioning and fixation in six degrees of freedom may also be utilized. For example, boss 80 may be asymmetrical, thereby eliminating the requirement for pin 84, and threaded fastener 82 could be another form of fastener and located outside of boss 80.

Boss 80 is a cylinder protruding from first end 72 and includes a passageway therethrough for extension of threaded fastener 82. Referring to FIG. 1B, mounting interface 79, defined on mounting block 54 of instrument 44, includes threaded bore 88 having a counterbore forming boss receptacle 86 for receiving boss 80 and threaded fastener 82 of instrument mounting interface 78. The dimensional tolerances of first end 72, boss 80, and boss receptacle 86 are sufficiently tight to provide accurate coupling in five degrees of freedom when instrument mounting interface 78 is coupled to mounting interface 79 and threaded fastener 82 secures support arm structure 42 to mounting block 54.

To accurately orient the sixth degree of freedom about axis 90 (FIG. 2A) extending through boss 80, pin 84, which is laterally offset from boss 80 and protrudes from first end 72, engages with tight tolerance into pin receptacle 92 of mounting interface 79 (FIG. 1B). Engagement of pin 84 into receptacle 92 completes the locating of support arm structure 42 relative to mounting block 54, and therefore cutting guide 52. First extension portion 70 defines cutout 94 in which knurled knob 96 for engaging threaded fastener 82 with threaded bore 88 (FIG. 1B) is disposed. Tightening fastener 82 to bore 88 completes the fixing of support arm structure 42 relative to mounting block 54.

Referring to FIG. 2B, second extension portion 74 of support arm structure 42 defines reference array mounting interface 98 at second end 76. Referring to FIGS. 2C and 2D, mounting interface 98, which defines oppositely facing dovetail portions 102 and 104 (FIG. 2D), engages support arm structure 42 to mounting interface 100, which defines dovetail receptacle 101, of reference array 46. Mounting interfaces 98 and 100 are designed to accurately position and couple support arm structure 42 and reference array 46 in a predefined geometry.

Advantageously, array mounting interface 98 defines top and bottom male dovetail portions 102 and 104, each of which are receivable by female dovetail receptacle 101 (FIG. 2D) defined by mounting interface 100 of reference array 46.

Oppositely oriented dovetails 102 and 104 meet at intersection 110 (FIGS. 2B and 2D). Referring to FIG. 2B, second extension portion 74 tapers along top and bottom dovetails 102 and 104 in the direction of second end 76. Additionally, second extension portion 74 widens between both intersection 110 and top surface 106 (defining top dovetail 102) and intersection 110 and bottom surface 108 (defining bottom dovetail 104). Thus, as top or bottom dovetail 102 or 104 is received into oppositely tapered female dovetail 101 (FIG. 2D), a tightly toleranced locking arrangement is provided. Additionally, second end 76 of support arm structure 42 defines threaded hole 112 for receiving fastener 114 of reference array 46 (FIG. 2C), thereby accurately positioning and fixing second end 76 against stop 116 defined in reference array 46 at the interior end of mounting interface 100.

Figure 2E:
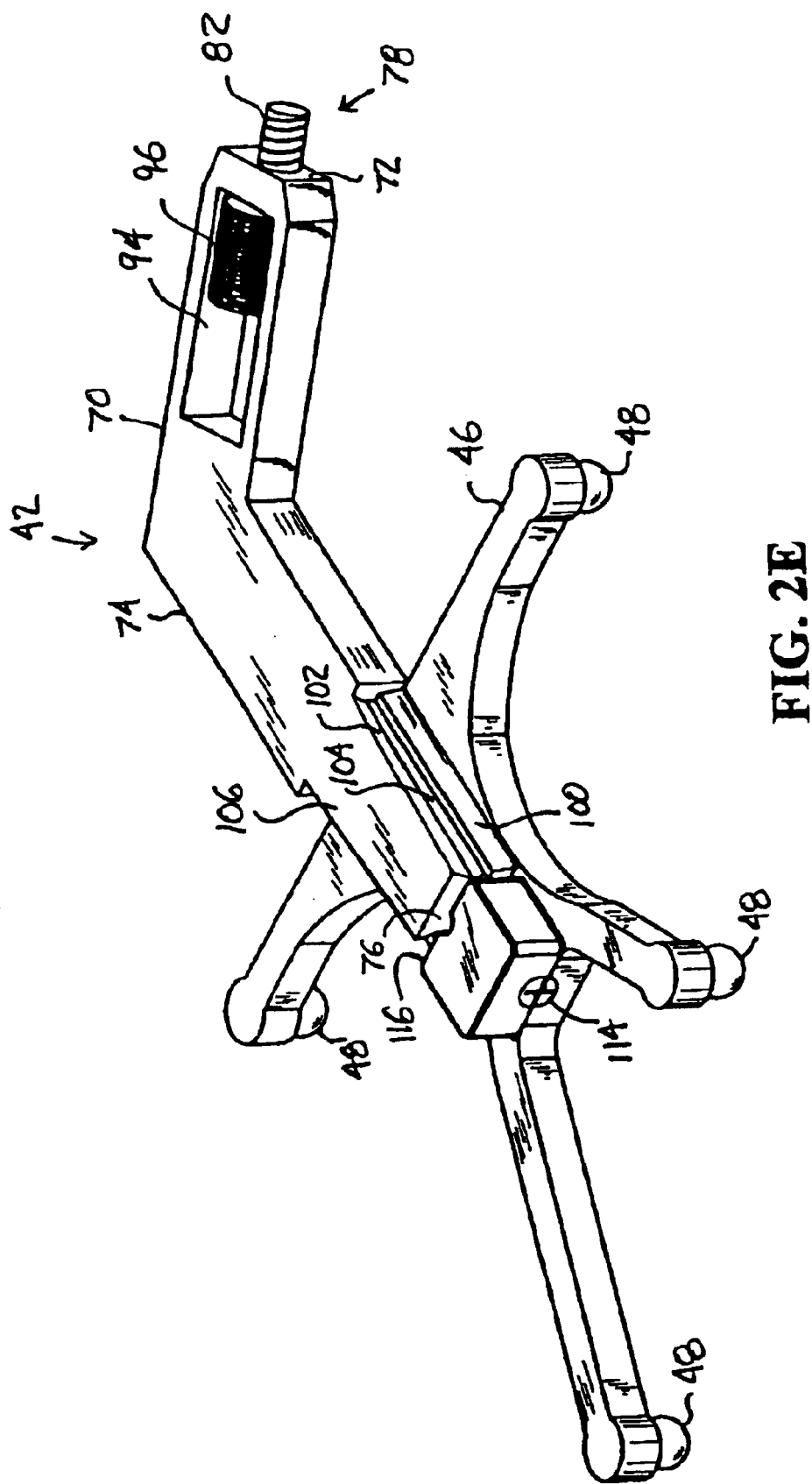

Similar to the coupling of instrument mounting interface 78 with mounting interface 79, mounting interface 98 and 100 provide a releasable and repeatably accurate coupling with a predefined geometry between reference array 46 and support arm structure 42. Advantageously, the double dovetail design in combination with a support arm structure that is nonlinear, i.e., includes first portion 70 and second portion 74 offset by approximately 45°, provides a single support arm structure that may be used to extend and offset reference array 46 from instrument 44 in two predefined positional geometries, as can be understood by comparing FIGS. 2C and 2E. In FIG. 2C, surface 106 (FIG. 2D) faces array 46 and dovetail 102 is engaged with dovetail receptacle 101 (FIG. 2D) of mounting receptacle 100, resulting in the illustrated geometry of first end 72 relative to array 46. In FIG. 2E, surface 108 (FIG. 2D) faces array 46 and dovetail 104 is engaged with dovetail receptacle 101 of mounting interface 100, resulting in the illustrated different geometry of first end 72 relative to array 46.

Support arm structure 42 advantageously provides a means of releasably fixing reference array 46 relative to instrument 44 in a predefined geometry, thereby eliminating the requirement to calibrate surgical instrument 44 with navigation system 20 each time surgical instrument 44 is employed. Calibration typically includes verifying the location of multiple landmarks on an instrument. Instead, apparatus 40 formed by reference array 46, support arm structure 42, and instrument 44 need only be registered by a verification process that allows navigation system 20 to determine which of the two predefined geometries defined by top and bottom dovetails 102 and 104 are being utilized and to ensure no component has been bent or otherwise damaged. For example, verification may involve verifying the location of only one landmark on instrument 44.

Referring to FIG. 1B, in the exemplary procedure for preparing the tibial plateau, using navigation system 20 to position tibial cutting guide 52 relative to anatomical structures of patient 34, extramedullary frame 60 provides support for instrument 44 while support arm structure 42 and reference array 46 aid the positioning of cutting guide 52. The location and orientation of cutting guide 52 is determined by navigation system 20, thereby providing for display of the geometry of cutting guide 52 relative to anatomical structures of patient 34.

Note that for the lateral approach to right knee 50 illustrated by FIG. 1B the positional engagement and shape of support arm 42 positions reference array 46 parallel to supinely oriented patient 34 and medially of cutting guide 52 so that reference elements 48 are accessible to reference locator 28 and do not encumber the surgeon. Advantageously, for a medial approach to right knee 50 or a lateral approach to left knee 120 (FIG. 1A), reference array 46 would be coupled to the bottom dovetail 104 rather than the top dovetail 102 as shown, and support arm structure 42 would be coupled to mounting interface 79 adjacent the mounting interface that support arm structure 42 is shown coupled to in FIG. 1B, thereby again positioning reference array 46 parallel to supinely oriented patient 34, including locating reference array 46 above the tibia (not shown) and away from cutting guide 52 and anatomical structures of patient 34.

Although the anatomical structures of patient 34 are generally represented on display 22 of navigation system 20 by a graphical model that may include a fluoroscopic image of anatomical structures, other methods of display may be used, such as acquiring a series of two-dimensional images of anatomical structures of patient 34 and modeling a three-dimensional form that may then be used to generate displays of anatomical structures for various perspectives for preoperative planning purpose and intraoperative navigational purposes.

A variety of technologies which may be employed to generate such a model of the anatomical structure are well known in the art and include computed tomography (CT), magnetic resonance imaging (MRI), positron emission tomography (PET), ultrasound scanning, and fluoroscopic imaging technologies. The model of the anatomical structures of patient 34 obtained by such imaging technology can be used for the intraoperative guidance of an instrument such as instrument 44 by facilitating the determination and display of the relative position and orientation of instrument 44 with respect to one or more actual anatomical structures. For example, if the model of the relevant anatomical structure is a set of two-dimensional images having known spatial relationships, several such images may be simultaneously displayed during the surgical procedure. By also displaying the position of instrument 44 in the images and displaying the images taken from different perspectives, e.g., one image facilitating the display of instrument 44 moving along the Y coordinating axis and another image facilitating the display of instrument 44 movement along the Z axis, the individual images may together represent the movement of instrument 44 in three dimensions. The illustrated embodiment of the present invention may be utilized without displaying movement of instrument 44 in all three dimensions. A coordinate system defined by the actual anatomical structure includes data concerning the fixed size and shape of instrument 44, or a relevant portion thereof, which will be used in the image-guided procedure and also to predefine the geometry of reference array 46 and support arm structure 42 relative to cutting guide 52, thereby allowing processor 24 to locate and position cutting guide 52 relative to anatomical structures of patient 34.

Registration of both anatomical structures and instrument 44 allows relative position and orientation of instrument 44 to be communicated to the surgeon by displaying images of anatomical structures of patient 34 and instrument 44 based on the three-dimensional models of anatomical structures of patient 34 and instrument 44. Additionally, relative positions may be displayed on display 22 using numerical or graphic information other than two or three-dimensional modeling that may aid the surgeon in properly locating instrument 44 relative to the anatomical structure(s).

In the exemplary embodiments reference elements 48 are passive, reflecting infrared light from source 30 (FIG. 1A) to sensors 32. Alternatively, reference elements 48 may also be active, for example, infrared emitters detectable by sensors 32. Other localizing systems, e.g., radiofrequency or visible light systems, may also be used.

Figure 3A:
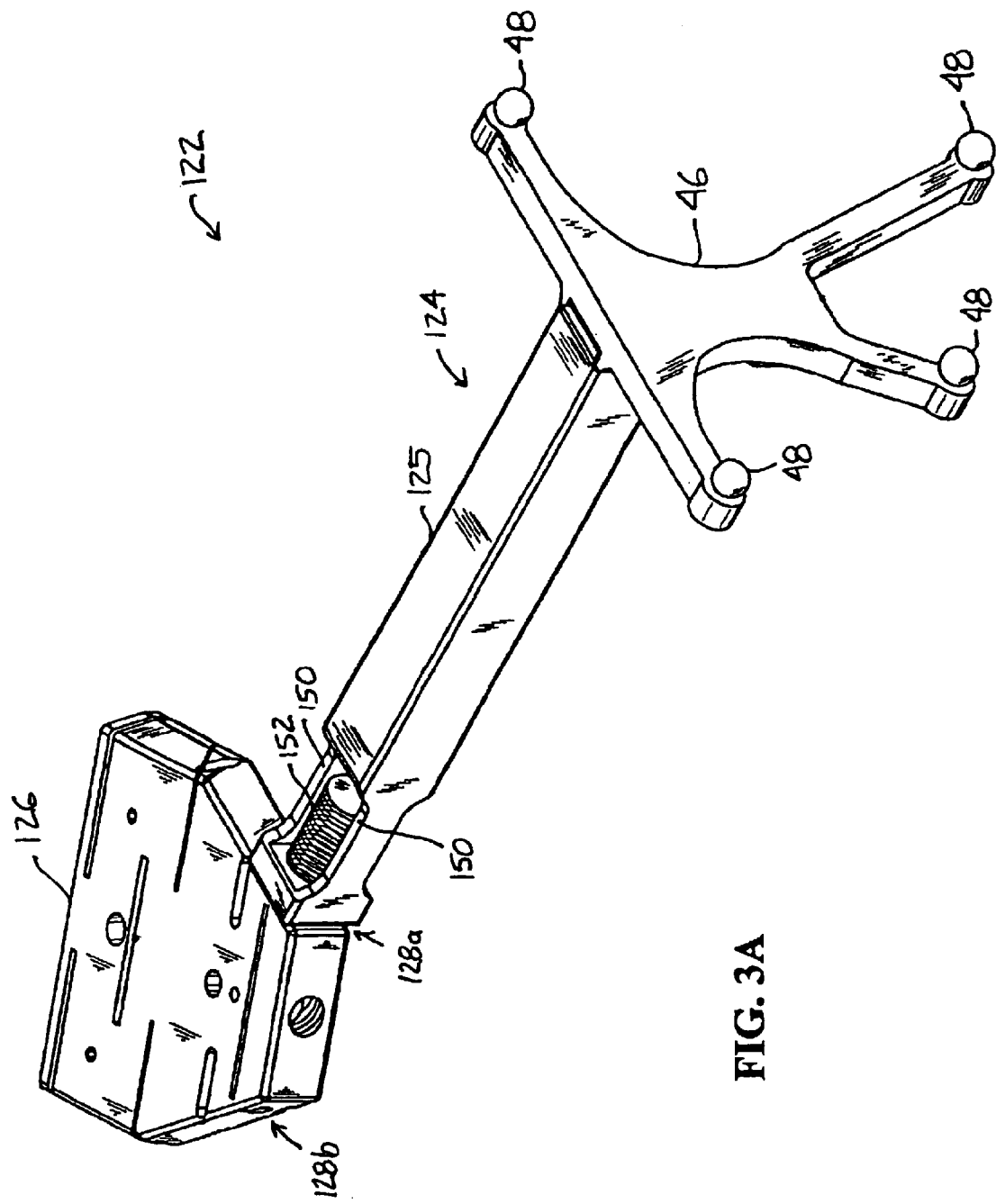
FIGS. 3A and 3B are perspective views of a surgical apparatus including a second embodiment support arm structure according to the present invention.
Figure 3B:
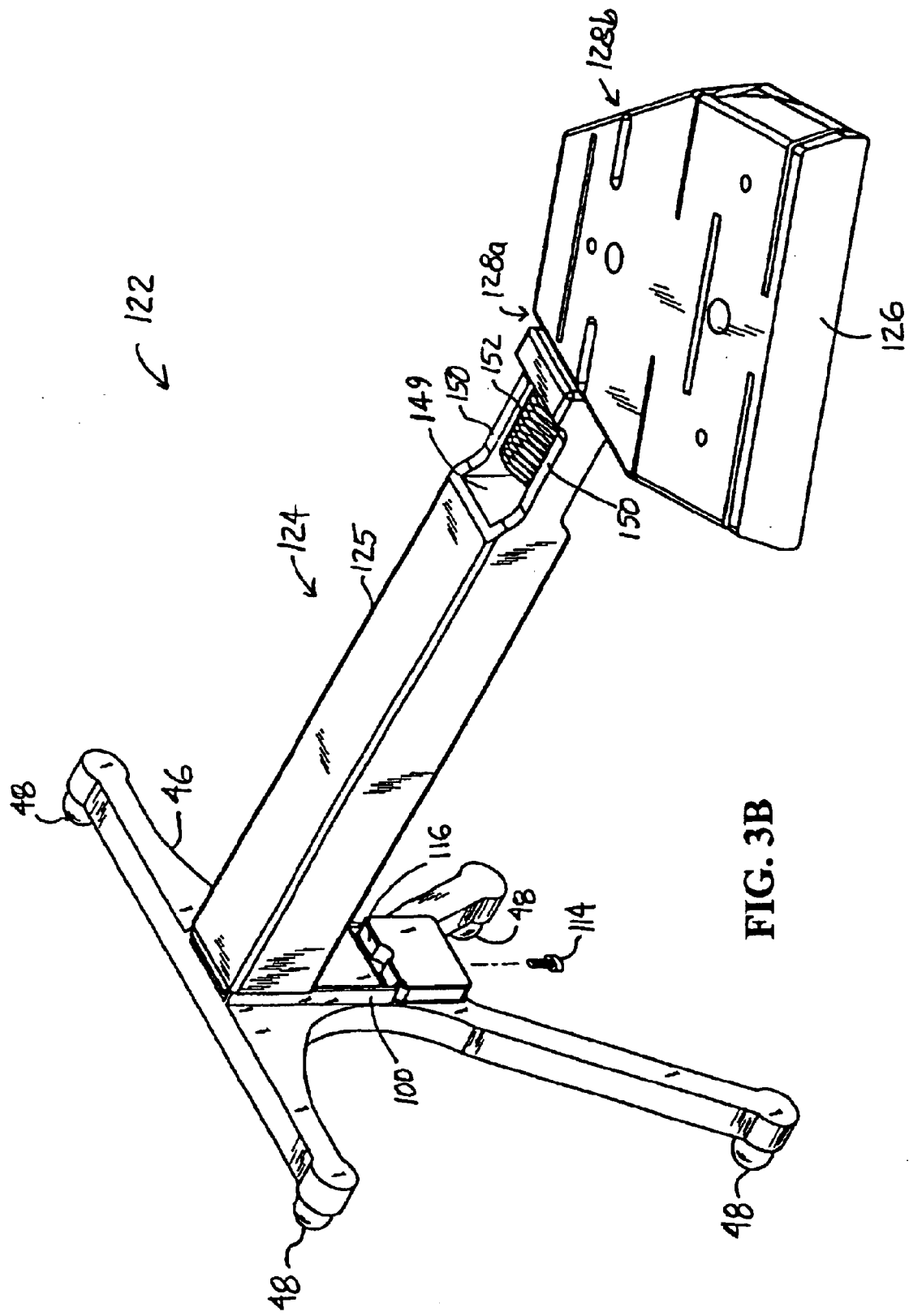

Referring to FIGS. 3A and 3B, apparatus 122 includes second exemplary embodiment support arm structure 124 for coupling instrument 126, in this embodiment a femoral profile cut guide, and reference array 46. Support arm structure 124 may be coupled to either one of two predefined positions 128a and 128b, thereby providing an option to the surgeon for the direction of offset in which reference array 46 is oriented relative to instrument 126. Support arm structure 124 may be advantageously designed especially for use with surgical instrument 126 and may include mounting interface 130, shown in FIG. 4B. Mounting interface 130 is designed to only physically be couplable with a matching mounting interface located at predetermined positions 128a and 128b of instrument 126. Alternatively, support arm structure 124 may be designed to be coupled with a number of different surgical instruments, thereby reducing the number of reference arrays 46 and support arm structures 124 necessary to complete surgical procedures.

Figure 4A:
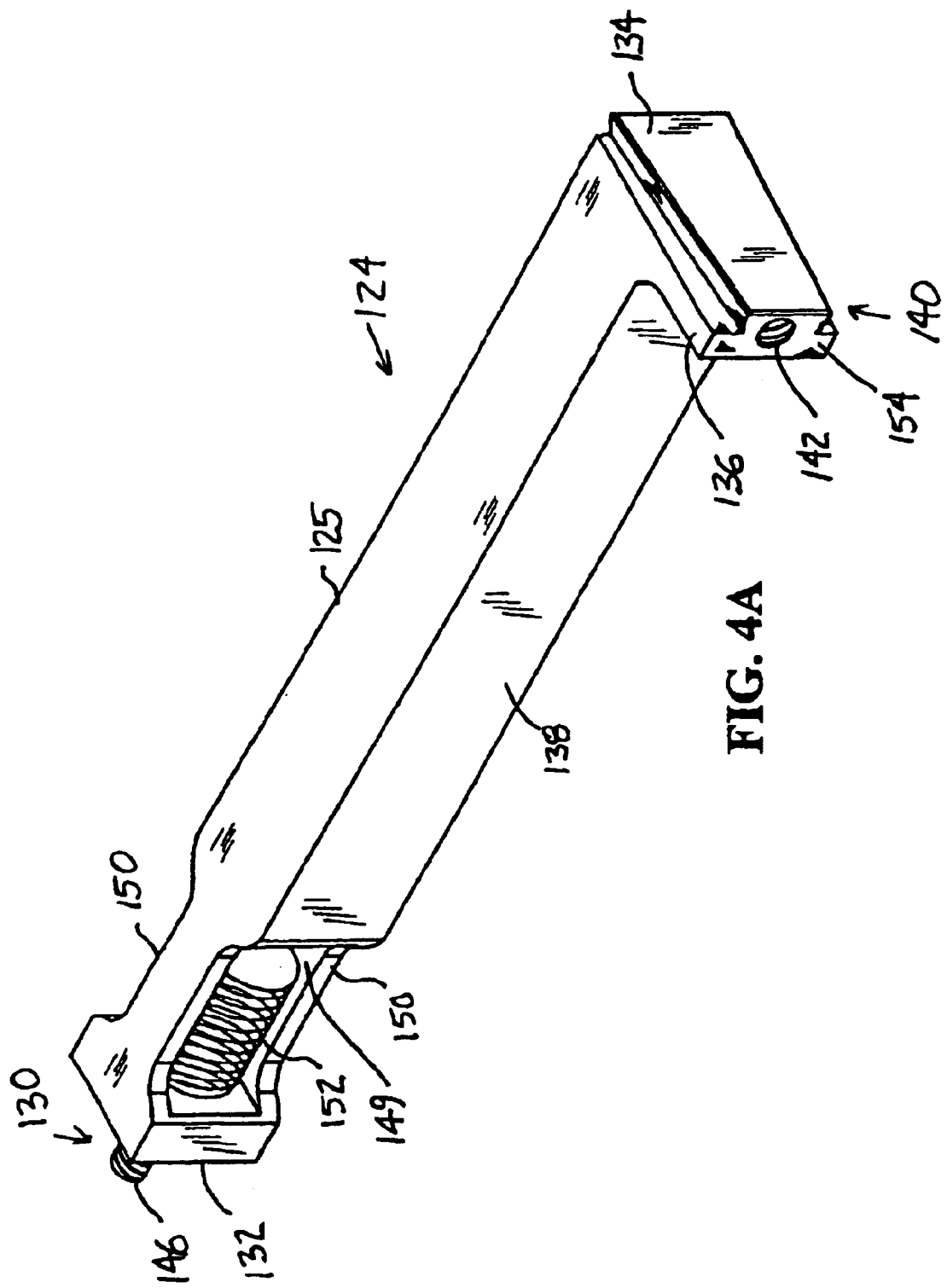
FIGS. 4A and 4B are perspective views of a second embodiment support arm structure shown in FIGS. 3A and 3B.
Figure 4B:
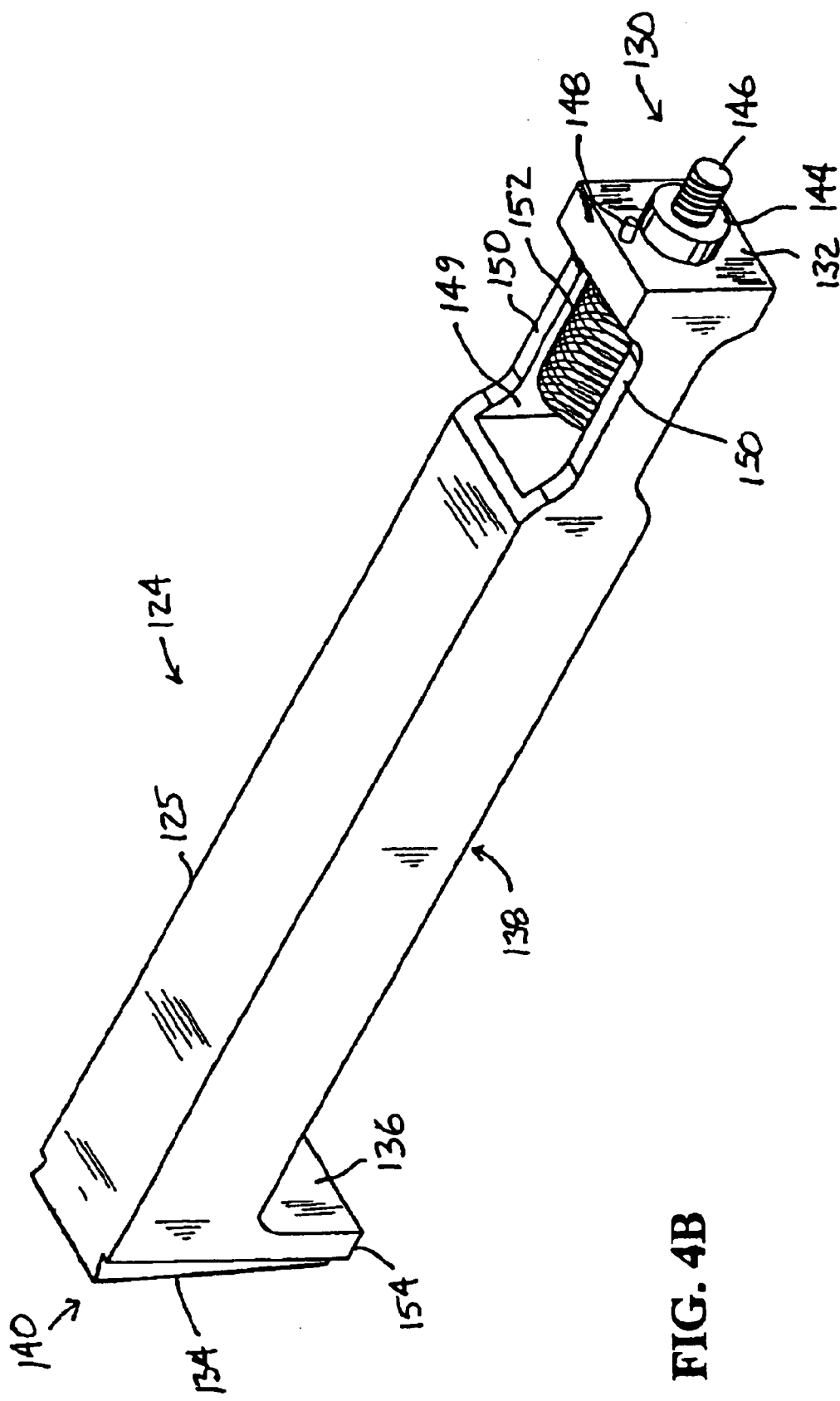

Referring to FIGS. 4A and 4B, second exemplary embodiment support arm structure 124 has body 125 generally in the shape of a rectangular bar and having a first end 132 upon which mounting interface 130 is disposed. An opposite second end 134 defines rectangular extension 136 oriented 90° to body 125 and extending downward in the direction of bottom surface 138 of support arm structure 124. Second end 134 defines male dovetail mounting interface 140 and threaded receptacle 142 thereon.

Referring to FIG. 4B, first end 132 includes mounting interface 130 for coupling support arm structure 124 to instrument 126 (FIGS. 3A and 3B) in a releasable and repeatably accurate predefined geometry. Mounting interface 130 may include cylindrical boss 144 protruding from first end 132 and having threaded fastener 146 passing therethrough, and rotational locating pin 148 protruding from first end 132 and laterally adjacent to boss 144. Mounting interface 130 functions as described for instrument mounting interface 78 (FIG. 2A) discussed above.

Support arm structure 124 may also define opening 149 forming links 150 on opposite sides and connecting first end 132 to body 125 of support arm structure 124. Knurled knob 152 for rotatably engaging threaded fastener 146 is disposed in opening 149.

Referring to FIGS. 4A and 4B, male dovetail mounting interface 140 is tapered and otherwise shaped similar to each of top and bottom dovetail 102 and 104 (FIG. 2B) and releasably and repeatably accurately engages mating female dovetail mounting interface 100 (FIG. 2D) defined by reference array 46. Threaded receptacle 142 defined in second end 134 (FIG. 4A) is used to draw end surface 154 of rectangular extension 136 against stop 116 (FIG. 3B) of reference array 46. The engagement of dovetails 140 and 100 and end surface 154 (FIG. 4A) and stop 116 (FIG. 3B) provide a releasable and repeatedly accurate predefined geometry between support arm structure 124 and reference array 46, and therefore between instrument 126 and reference array 46. This arrangement is similar to the predefined geometry provided by the coupling of first embodiment support arm structure 42 with surgical instrument 44 and reference array 46.

Figure 5A:
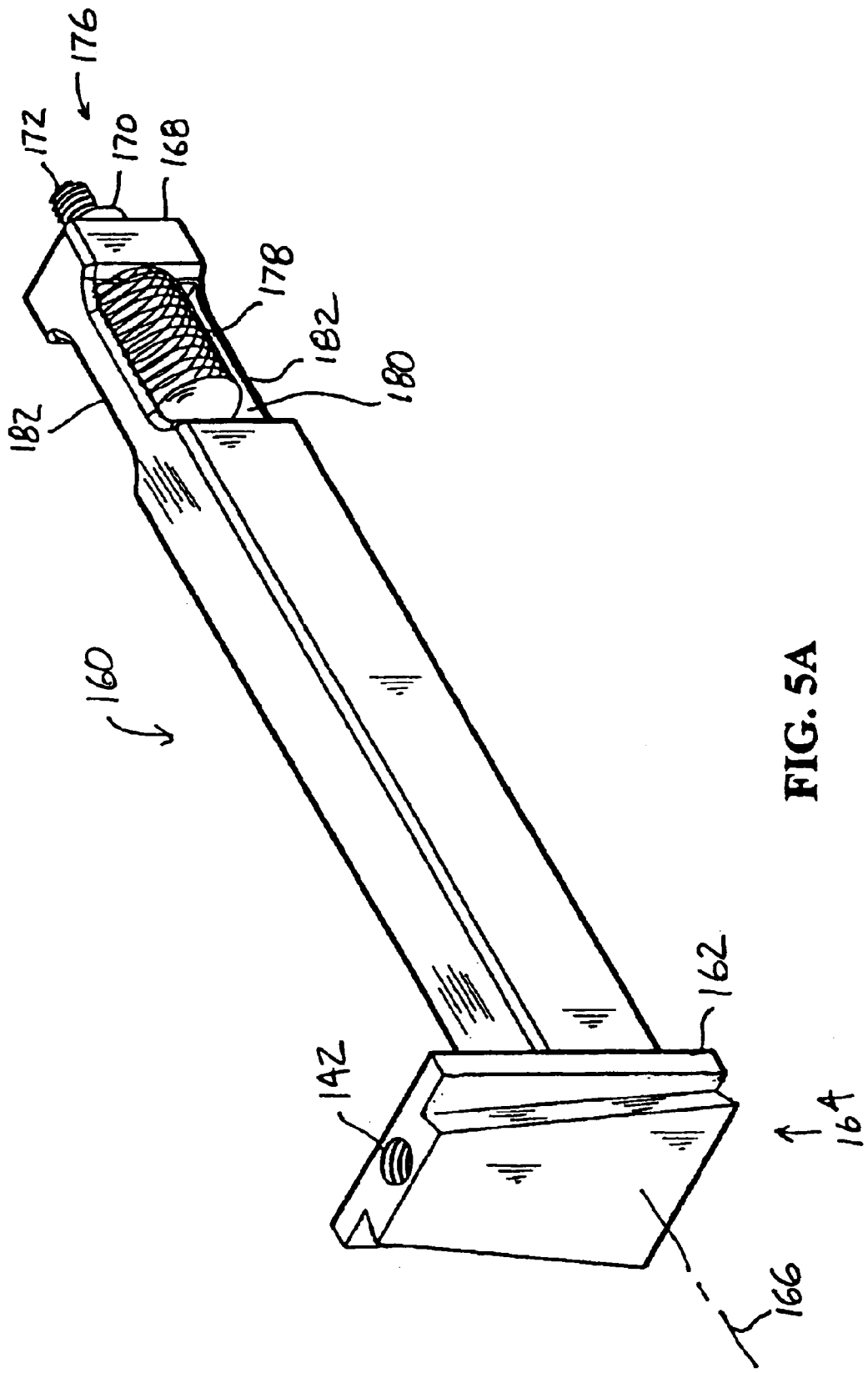
FIGS. 5A and 5B are perspective views of a third embodiment support arm structure according to the present invention.
Figure 5B:
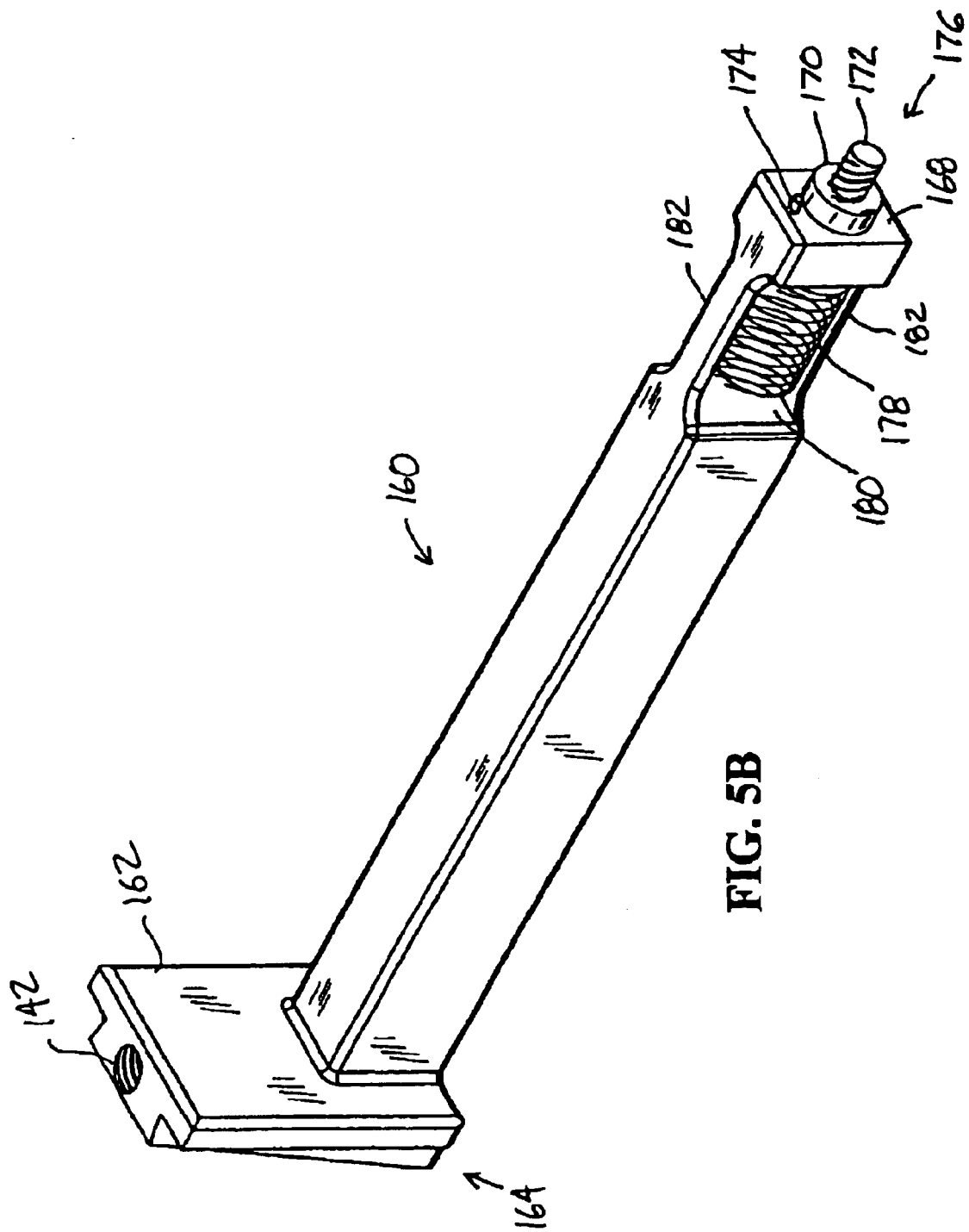

Third embodiment support arm structure 160 shown in FIGS. 5A and 5B is similar in design to second exemplary embodiment support arm 124 shown in FIGS. 4A and 4B. One exception is that rectangular extension 162, upon which male dovetail mounting interface 164 and threaded receptacle 142 are defined, is oriented 90° relative to longitudinal axis 166 from the orientation of dovetail 140 of second embodiment support arm structure 124 shown in FIGS. 4A and 4B. Additionally, referring to FIG. 5B, as can be seen at first end 168 which is located opposite rectangular extension 162, support arm structure 160 is narrower along at least one axis and is therefore more rectangular in cross-section than second embodiment support arm structure 124, shown most clearly at first end 132 of FIG. 4B. Similar to first and second embodiment support arm structures 42 and 124, first end 168 of third embodiment support arm structure 160 includes boss 170, threaded fastener 172 and rotational locating pin 174 defining instrument mounting interface 176. Also, knurled knob 178 is disposed in cutout 180 formed by oppositely located links 182.

The length, shape, and other aspects of support arm structure 160, including the particular geometry of mounting interface 176 and 164, may be configured as desired to provide the necessary displacement, offset and engagement required for a specific surgical instrument and procedure for which it is designed.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. An apparatus usable with a computer-assisted navigation system, the apparatus comprising:
    an instrument;
    a support structure releasably engageable with said instrument in a first predefined position and defining two adjacent and oppositely oriented dovetail-shaped projections having a common distal end, said distal end defining a fastener receptacle;
    at least one reference element connected to said support structure in a second predefined position, said at least one reference element being registrable in the computer-assisted navigation system;
    said first and second predefined positions and said support structure comprising a first predefined geometry of said at least one reference element relative to said instrument in each of six degrees of freedom; and
    a reference array releasably securable to said support structure in a third predefined position and defining a dovetail-shaped recess, said first, second, and third predefined positions and said support structure comprise a second predefined geometry of said reference array relative to said instrument in each of six degrees of freedom; wherein said reference array includes a fastener and is selectively mountable on one of said dovetail-shaped projections and is securable thereon by engagement of said fastener with said fastener receptacle upon said dovetail-shaped recess being engaged with either of said dovetail-shaped projections.

2. The apparatus of claim 1, wherein:
    said instrument includes a first mounting interface;
    said support structure includes a second mounting interface; and
    coupling of said first and said second mounting interfaces engages said support structure releasably with said instrument in said first predefined geometry.

3. The apparatus of claim 2 further comprising a reference array wherein said at least one reference element comprises at least three nonlinearly disposed reference elements disposed with said reference array, said reference array being releasably securable to said support structure in at least one additional predefined position; and wherein each of said at least one additional predefined positions define another predefined geometry of said reference array relative to said instrument in each of six degrees of freedom.

4. The apparatus of claim 3 wherein said support structure comprises a bar having two opposite ends and a third mounting interface for releasably coupling said reference array, said third mounting interface being disposed at one of said opposite ends.

5. The apparatus of claim 2 wherein said at least one reference element comprises at least three nonlinearly disposed reference elements.

6. The apparatus of claim 5 wherein said at least three reference elements are disposed with said reference array.

7. An apparatus usable with a computer-assisted navigation system, the apparatus comprising:
    an instrument including a first mounting interface;
    a support structure releasably engageable with said instrument in a first predefined position and including a second mounting interface; and
    at least one reference element connected to said support structure in a second predefined position, said at least one reference element being registrable in the computer-assisted navigation system;
    said first and second predefined positions and said support structure comprising a first predefined geometry of said at least one reference element relative to said instrument in each of six degrees of freedom;
    wherein one of said first and said second mounting interfaces comprise at least one recess and the other of said first and said second mounting interface comprises at least one projection engageable with said at least one recess;
    wherein said first mounting interface and said second mounting interface define a mounting axis, said at least one recess and said at least one projection being nonsymmetrical about said mounting axis; and wherein engagement of said at least one recess and said at least one projection rotationally fixes said support structure relative to said instrument about said mounting axis.

8. The apparatus of claim 7 wherein said support structure comprises a bar having two opposite ends, and said second mounting interface is disposed at one of said opposite ends.

9. An apparatus usable with a computer-assisted navigation system, the apparatus comprising:
    an instrument including a first mounting interface;
    a support structure releasably engageable with said instrument in a first predefined position and including a second mounting interface; and at least one reference element connected to said support structure in a second predefined position, said at least one reference element being registrable in the computer-assisted navigation system;

said first and second predefined positions and said support structure comprising a first predefined geometry of said at least one reference element relative to said instrument in each of six degrees of freedom;

wherein one of said first and said second mounting interfaces comprise at least one recess and the other of said first and said second mounting interface comprises at least one projection engageable with said at least one recess;

wherein said at least one recess comprises at least two noncoaxial recesses and said at least one projection comprises at least two noncoaxial projections engageable with said at least two noncoaxial recesses.

10. The apparatus of claim 9 wherein one of said at least two noncoaxial recesses further comprises a threaded receptacle and one of said at least two noncoaxial projections further comprises a threaded fastener engageable with said threaded receptacle.

11. An apparatus useable to enable an instrument to be used with a computer-assisted navigation system, the apparatus comprising:

a support structure releasably engageable with the instrument in a first predefined position;

at least one reference element disposed with said support structure in a second predefined position, said at least one reference element being registrable in the computer-assisted navigation system; and a reference array and wherein said at least one reference element is disposed with said reference array, said reference array being releasably securable to said support structure in said second predefined position; wherein said reference array defines a dovetail-shaped recess and said support structure defines two adjacent and oppositely oriented dovetail-shaped projections having a common distal end, said distal end defining a fastener receptacle, wherein said reference array includes a fastener and is selectively mountable on one of said dovetail-shaped projections and is securable thereon by engagement of said fastener with said fastener receptacle upon said dovetail-shaped recess being engaged with either of said dovetail-shaped projections;

said first and second predefined positions determining a first predefined geometry of said at least one reference element relative to the instrument in each of six degrees of freedom.

12. The apparatus of claim 11 wherein said support structure includes a first mounting interface for releasably engaging said support structure with the instrument in said first predefined position, thereby forming said first predefined geometry.

13. The apparatus of claim 12 wherein said at least one reference element comprises at least three nonlinearly disposed reference elements.

14. The apparatus of claim 12 wherein said first and second predefined positions defining a second predefined geometry of said at least one reference element to said instrument in each of six degrees of freedom.

15. The apparatus of claim 12 wherein said at least one reference element comprises at least three nonlinearly disposed reference elements disposed with said reference array, said reference array being releasably securable to said support structure in at least one additional predefined position; and wherein each of said at least one additional predefined positions define another predefined geometry of said reference array relative to the instrument in each of six degrees of freedom.

16. The apparatus of claim 15 wherein said support structure comprises a nonlinear bar having two opposite ends and a second mounting interface for releasably coupling said reference array, said second mounting interface being disposed at one of said opposite ends.

17. An apparatus useable to enable an instrument to be used with a computer-assisted navigation system, the apparatus comprising:

a support structure releasably engageable with the instrument in a first predefined position and including a first mounting interface for releasably engaging said support structure with the instrument in said first predefined position; and at least one reference element disposed with said support structure in a second predefined position, said at least one reference element being registrable in the computer-assisted navigation system;

said first and second predefined positions determining a first predefined geometry of said at least one reference element relative to the instrument in each of six degrees of freedom;

wherein said first mounting interface comprises at least two noncoaxial projections engageable with the instrument.

18. The apparatus of claim 17 wherein said support structure comprises a bar having two opposite ends, and said first mounting interface is disposed at one of said opposite ends.

19. The apparatus of claim 17 wherein at least one of said at least two noncoaxial projections comprises a threaded fastener engageable with the instrument.

20. A method of preparing an instrument having a first predefined geometry for registration in a computer-assisted navigation system, said method comprising the steps of:

providing a support structure which is accurately and releasably engageable to the instrument in only a second predefined geometry relative to the instrument;

providing a reference array having at least one reference element disposed therewith, said reference element having a third predefined geometry and being registrable in the computer-assisted navigation system;

providing said first, second, and third predefined geometries to the computer-assisted navigation system;

releasably coupling said support structure to the instrument; and releasably coupling said reference array to said support structure in a fourth predefined geometry;

wherein said first, second, third and fourth predefined geometry define a known spatial relationship of said at least one reference element and the instrument in the computer-assisted navigation system; and wherein said reference array defines a dovetail-shaped recess and said support structure defines two adjacent and oppositely oriented dovetail-shaped projections having a common distal end, said distal end defining a fastener receptacle, wherein said reference array includes a fastener and is selectively mountable on one of said dovetail-shaped projections and is securable thereon by engagement of said fastener with said fastener receptacle upon said dovetail-shaped recess being engaged with either of said dovetail-shaped projections.

21. The method of claim 20, wherein the step of releasably coupling said support structure to said instrument comprises:

engaging a first mounting interface of the instrument to a second mounting interface of said support structure in a second predefined geometry.

22. The method of claim 21 wherein the step of engaging said first and second mounting interfaces comprises:

engaging at least one projection with at least one recess.

23. The method of claim 22 wherein the step of engaging at least one projection comprises:

engaging a threaded portion of said projection with a threaded portion of said recess.

24. The method of claim 21, further comprising the steps of:

providing a third mounting interface on the instrument in a third predefined position; and removably securing said support structure to said instrument by engaging said second and third mounting interfaces.

25. The method of claim 21, further comprising the step of:

providing a third mounting interface on said support structure, said third mounting interface for releasably coupling said reference array to said support structure, and said third mounting interface having a plurality of predefined positions to which said reference array may be releasably coupled.

26. The method of claim 21, further comprising the step of:

engaging one of said two adjacent and oppositely oriented dovetail-shaped projections defined by said support structure with said dovetail-shaped recess defined by said reference array.

* * * * *